United States Patent [19]

Ksander et al.

[11] Patent Number: 4,962,105
[45] Date of Patent: Oct. 9, 1990

[54] POTENTIATION OF ANTIHYPERTENSIVE EFFECT OF ACE INHIBITORS

[75] Inventors: Gary M. Ksander, Milford; Mark B. Zimmerman, Springfield, both of N.J.

[73] Assignee: Ciba-Geigy Corporation, Ardsley, N.Y.

[21] Appl. No.: 109,965

[22] Filed: Oct. 19, 1987

[51] Int. Cl.$^5$ .................... A61K 31/55; C07D 223/6
[52] U.S. Cl. .................................................... 514/212
[58] Field of Search ................... 514/332, 212; 260/239.3 B; 424/263, 273 R; 546/270, 273; 548/336

[56] References Cited

U.S. PATENT DOCUMENTS

| | | | |
|---|---|---|---|
| 4,473,575 | 10/1984 | Watthey | 424/263 |
| 4,478,842 | 4/1984 | Renfroe | 424/263 |
| 4,511,573 | 6/1985 | Renfroe | 514/332 |
| 4,575,503 | 3/1986 | Watthey | 260/239 B |
| 4,600,534 | 1/1986 | Bach et al. | 260/239.3 B |

FOREIGN PATENT DOCUMENTS 0219782 10/1986 European Pat. Off.

OTHER PUBLICATIONS

Chiba, et al., Abstract 07–18 Kyoto Conference on Prostoglandins, Nov. 25–28 (1984).
Weir et al., Am. J. Hypertension, vol. 1, No. 3, part 2, (1989), Abstract No. 1014, p. 69A.
USAN 1989, p. 444.
Bitterman et al., J. Pharmacology Exp. Ther., vol. 242, pp. 8–14, (1987).
Cross et al., Annual Reports in Medicinal Chemistry, vol. 22, 95–105 (1987).
Cardiovascular Drugs and Therapy, vol. 1, No. 3, p. 223 (10/87).

*Primary Examiner*—Prince E. Willis
*Assistant Examiner*—John F. McNally
*Attorney, Agent, or Firm*—Norbert Gruenfeld

[57] ABSTRACT

Disclosed is a method of enhancing the antihypertensive effect of an angiotensin converting enzyme inhibitor which comprises the administration to mammals of an effective antihypertensive potentiating amount of 1-(7-carboxyheptyl)-3-methyl-2-(3-pyridyl)-indole, 1-methyl-2-(3-pyridyl)-3-)5-carboxypentyl)-5-chloroindole, or a pharmaceutically acceptable salt thereof. Also disclosed are pharmaceutical compositions comprising the 2-(3-pyridyl)-indole derivatie in combination with an angiotensin converting enzyme inhibitor.

16 Claims, No Drawings

POTENTIATION OF ANTIHYPERTENSIVE EFFECT OF ACE INHIBITORS

SUMMARY OF THE INVENTION

The present invention concerns the discovery that the 2-(3-pyridyl)-indole derivatives 1-(7-carboxyheptyl-3-methyl-2-(3-pyridyl)-indole and 1-methyl-2-(3-pyridyl)-3-(5-carboxypentyl)-5-chloroindole or pharmaceutically acceptable salts thereof potentiate the antihypertensive effect of ACE (angiotensin converting enzyme) inhibitor antihypertensive agents.

More particularly the invention is directed to a method of potentiating the antihypertensive effect of an angiotensin converting enzyme inhibitor in a mammal being treated with an angiotensin converting enzyme inhibitor by administering to said mammal in need of such potentiation an effective antihypertensive potentiating amount of 1-(7-carboxyheptyl)-3-methyl-2-(3-pyridyl)-indole or 1-methyl-2-(3-pyridyl)-3-(5-carboxypentyl)-5-chloroindole, or a pharmaceutically acceptable salt thereof or a pharmaceutical composition comprising a said compound in combination with one or more pharmaceutically acceptable carriers.

It is a further object of the invention to provide pharmaceutical compositions containing a combination of an effective antihypertensive amount of an angiotensin converting enzyme inhibitor and an amount effective for potentiating the antihypertensive effect of said angiotensin converting enzyme inhibitor of 1-(7-carboxyheptyl)-3-methyl-2-(3-pyridyl)-indole, 1-methyl-2-(3-pyridyl)-3-(5-carboxypentyl)-5-chloroindole or a pharmaceutically acceptable salt thereof, in combination with one or more pharmaceuticall acceptable carriers.

DETAILED DESCRIPTION OF THE INVENTION

The angiotensin converting enzyme inhibitors used as antihypertensive agents, the effect of which is potentiated, are those known in the art, e.g. captopril, enalapril, enalaprilat, quinapril, ramipril, cilazapril, delapril, fosenopril, zofenopril, indolapril, lisinopril, perindopril, spirapril, pentopril, pivopril, benazepril, benazeprilat, libenzapril and known pharmaceutically acceptable salts thereof. The names indicated are USAN (United States Adopted Names) or INN (International Non-Proprietary Names) adopted names.

As to benazepril, benazeprilat, libenzapril (as yet unpublished names), such compounds are also known in the art as CGS 14824, CGS 14831 and CGS 16617, respectively, and are 2,3,4,5-tetrahydro-1H-1-benzazepin-2-one derivatives of formula I.

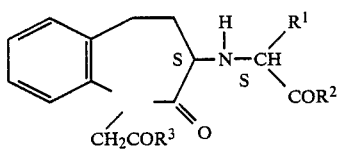

Benazepril (CGS 14824) is the compound of formula I wherein $R^1$ represents 2-phenylethyl, $R^2$ represents ethoxy, and $R^3$ represents hydroxy.

Benazeprilat (CGS 14831) is the compound of formula I wherein $R^1$ represents 2-phenylethyl, $R^2$ and $R^3$ represent hydroxy.

Libenzapril (CGS 16617) is the compound of formula I wherein $R^1$ represents 4-aminobutyl, and $R^2$ and $R^3$ represent hydroxy. Said compounds are described e.g. in U.S. Pat. Nos. 4,600,534, 4,575,503 and 4,473,575, the disclosures of all of which are incorporated herein by reference.

1-(7-carboxyheptyl)-3-methyl-2-(3-pyridyl)-indole, also designated as CGS 12970, is a known thromboxane synthetase inhibitor e.g. as disclosed in U.S. Pat. No. 4,478,842, the disclosure of which is incorporated herein by reference. 1-Methyl-2-(3-pyridyl)-3-(5-carboxypentyl)-5-chloroindole is a known thromboxane synthetase inhibitor e.g. as described in U.S. Pat. No. 4,511,573, the disclosure of which is also incorporated herein by reference. Pharmaceutical compositions thereof are described in said U.S. patents.

Pharmaceutically acceptable salts of the compounds cited herein represent particularly those known in the art for said compounds, including any pharmaceutically acceptable acid-addition salts for compounds having a basic amino group and pharmaceutically acceptable salts derived from pharmaceutically acceptable bases for acidic compounds having e.g. a free carboxy group. The compounds, including their salts, can also be used in the form of their hydrates.

Pharmaceutical compositions represent pharmaceuticall acceptable compositions which are suitable for enteral such as oral, and parenteral such as intravenous administration to mammals, including man, and which comprise an effective amount of the active ingredients in combination with one or more pharmaceutically acceptable carriers, e.g. as aqueous solutions for parenteral administration, or as tablets or capsules for oral administration. Such pharmaceutical compositions are prepared according to methods generally known in the art, e.g. as described in the above-cited patents incorporated herein by reference.

A particular aspect of the invention is directed to antihypertensive pharmaceutical compositions suitable for administration to a mammal comprising (a) an antihypertensive effective amount of an angiotensin converting enzyme inhibitor selected from captopril, enalapril, enalaprilat, quinapril, ramipril, cilazapril, delapril, fosenopril, zofenopril, indolapril, lisinopril, perindopril, spirapril, pentopril, pivopril, benazepril, benazeprilat and libenzapril, or a pharmaceutically acceptable salt thereof; and (b) 1-(7-carboxyheptyl)-3-methyl-2-(3-pyridyl)-indole or 1-methyl-2-(3-pyridyl)-3-(5-carboxypentyl)-5-chloroindole, or a pharmaceutically acceptable salt thereof, in an amount effective for potentiating the antihypertensive effect of said angiotensin-converting enzyme inhibitor; in combination with one or more pharmaceutically acceptable carriers.

Preferred are the above-cited compositions wherein the angiotensin converting enzyme inhibitor is selected from enalapril, enalaprilat, quinapril, ramipril, cilazapril, delapril, indolapril, perindopril, lisinopril, spirapril, benazepril, benazeprilat and libenzapril, or a pharmaceutically acceptable salt thereof.

Particular preferred are the above-cited compositions wherein the angiotensin converting enzyme inhibitor is benazepril, benazeprilat, libenzapril, or a pharmaceutically acceptable salt thereof.

Particular embodiments of said compositions are directed to:

1. antihypertensive pharmaceutical compositions suitable for administration to a mammal comprising (a) an antihypertensive effective amount of the angiotensin converting enzyme inhibitor benazepril or a pharmaceutically acceptable salt thereof; and (b) 1-(7-carboxyheptyl)-3-methyl-2-(3-pyridyl)-indole or a pharmaceutically acceptable salt thereof in an amount effective for potentiating the antihypertensive effect of said angiotensin converting enzyme inhibitor; in combination with one or more pharmaceutically acceptable carriers;

2. antihypertensive pharmaceutical compositions suitable for administration to a mammal comprising (a) an antihypertensive effective amount of the angiotensin converting enzyme inhibitor libenzapril or a pharmaceutically acceptable salt thereof; and(b) 1-(7-carboxyheptyl)-3-methyl-2-(3-pyridyl)-indole or a pharmaceutically acceptable salt thereof in an amount effective for potentiating the antihypertensive effect of said angiotensin converting enzyme inhibitor; in combination with one or more pharmaceutically acceptable carriers;

3. antihypertensive pharmaceutical compositions suitable for administration to a mammal comprising (a) an antihypertensive effective amount of the angiotensin converting enzyme inhibitor benazepril or a pharmaceutically acceptable salt thereof; and (b) 1-methyl-2-(3-pyridyl)-3-(5-carboxypentyl)-5-choloroindole or a pharmaceutically acceptable salt thereof in an amount of effective for potentiating the antihypertensive effect of said angiotensin converting enzyme inhibitor; in combination with one or more pharmaceutically acceptable carriers;

4. antihypertensive pharmaceutical compositions suitable for administration to a mammal comprising (a) an antihypertensive effective amount of the angiotensin converting enzyme inhibitor libenzapril or a pharmaceutically acceptable salt thereof; and (b) 1-methyl-2-(3-pyridyl)-3-(5-carboxypentyl)-5-chloroindole or a pharmaceutically acceptable salt thereof in an amount effective for potentiating the antihypertensive effect of said angiotensin converting enzyme inhibitor; in combination with one or more pharmaceutically acceptable carriers.

A further specific aspect of the invention is directed to a method of potentiating the antihypertensive effect of an angiotensin converting enzyme inhibitor in a mammal receiving an angiotensin converting enzyme inhibitor which comprises the administration to a mammal in need thereof of an effective potentiating amount of 1-(7-carboxyheptyl)-3-methyl-2-(3-pyridyl)-indole, 1-methyl-2-(3-pyridyl)-3-(5-carboxypentyl)-5-chloroindole, or a pharmaceutically acceptable salt thereof, or a pharmaceutical composition comprising a said compound in combination with one or more pharmaceutically acceptable carriers, said angiotensin converting enzyme inhibitor being selected from captopril, enalapril, enalaprilat, quinapril, ramipril, cilazapril, delapril, fosenopril, zofenopril, indolapril, lisinopril, perindopril, spirapril, pentopril, pivopril, benazepril, benazeprilat and libenzapril, or a pharmaceutically acceptable salt thereof.

Particular embodiments thereof are directed to:

1. a method as described above of potentiating the antihypertensive effect of an angiotensin-converting enzyme inhibitor selected from enalapril, enalaprilat, quinapril, ramipril, cilazapril, delapril, indolapril, perindopril, lisinopril, spirapril, benazepril, benazeprilat, libenzapril, or a pharmaceutically acceptable salt thereof;

2. a method of potentiating the antihypertensive effect of an angiotensin converting enzyme inhibitor selected from benazepril, benazeprilat, libenzapril or a pharmaceutically acceptable salt thereof, comprising the administration of an effective potentiating amount of 1-(7-carboxyheptyl)-3-methyl-2-(3-pyridyl)-indole, a pharmaceutically acceptable salt thereof or a pharmaceutical composition comprising a said compound;

3. a method of potentiating the antihypertensive effect of an angiotensin converting enzyme inhibitor selected from benazepril, benazeprilat and libenzapril, or a pharmaceutically acceptable salt thereof comprising the administration of an effective potentiating amount of 1-methyl-2-(3-pyridyl)-3-(5-carboxypentyl)-5-chloroindole, or a pharmaceutically acceptable salt thereof or a pharmaceutical composition comprising a said compound; 4. a method of potentiating the antihypertensive effect of benazepril or a pharmaceutically acceptable salt thereof comprising the administration of an effective potentiating amount of 1-(7-carboxyheptyl)-3-methyl-2-(3-pyridyl)-indole, a pharmaceutically acceptable salt thereof or a pharmaceutical composition comprising a said compound; 5. a method of potentiating the antihypertensive effect of libenzapril or a pharmaceutically acceptable salt thereof comprising the administration of an effective potentiating amount of 1-(7-carboxyheptyl)-3-methyl-2-(3-pyridyl)-indole, a pharmaceutically acceptable salt thereof or a pharmaceutical composition comprising a said compound; 6. a method of potentiating the antihypertensive effect of benazepril or a pharmaceutically acceptable salt thereof comprising the administration of an effective potentiating amount of 1-methyl-2-(3-pyridyl)-3-(5-carboxypentyl)-5-chloroindole, a pharmaceutically acceptable salt thereof or a pharmaceutical composition comprising a said compound; 7. a method of potentiating the antihypertensive effect of libenzapril or a pharmaceutically acceptable salt thereof comprising the administration of an effective potentiating amount of 1-methyl-2-(3-pyridyl)-3-(5-carboxypentyl)-5-chloroindole, a pharmaceutically acceptable salt thereof or a pharmaceutical composition comprising a said compound.

The antihypertensive potentiating properties as defined above for the 2-(3-pyridyl)-indole derivatives are demonstrated using test procedures standard in the art for determining antihypertensive activity using advantageously mammals, such as rats or dogs. The antihypertensive potentiating compound, the 2-(3-pyridyl)-indole derivative as defined above, can be administered to the test animal enterally or parenterally, advantageously orally or intravenously, for example in the form of suspensions or aqueous solutions. For example, the oral dosage may range between about 0.1 and 25 mg/Kg, preferably between about 1 and 15 mg/Kg, the dose depending on the compound and mammal involved.

The antihypertensive potentiating compounds, the 2-(3-pyridyl)-indole derivatives as defined above, may be administered preferably prior to or simultaneously with the ACE inhibitor antihypertensive agent to be potentiated. Effective antihypertensive doses of the known ACE inhibitors are reported in the art or can be readily determined. The use of the lowest effective dose is preferred.

More particularly, the antihypertensive potentiating effect can be determined in male spontaneous hypertensive rats and the mean arterial pressure is measured in conscious fully ambulatory animals at intervals for 24 hours after administration of the 2-(3-pyridyl)-indole derivative. The blood pressure lowering effect after administration of the ACE inhibitor antihypertensive is compared to animals treated with the ACE inhibitor alone, the 2-(3-pyridyl)indole derivative alone and vehicle alone.

Illustrative of the invention, 1-(7-carboxyheptyl)-3-methyl-2-(3-pyridyl)-indole (CGS 12970) administered at a dose of 10 mg/Kg p.o. significantly potentiates the blood pressure lowering effect of libenzepril also administered at a dose of 10 mg/Kg p.o. to spontaneously hypertensive rats. For example at 5 hours post administration, the blood pressure is reduced by about 35 mm in animals administered both compounds. In contrast thereto, the blood pressure is reduced by only about 22 mmHg in animals administered libenzapril alone at the same dose of 10 mg/Kg p.o., and no blood pressure lowering effect is observed in animals administered CGS 12970 alone at the same dose of 10 mg/Kg p.o.. Under similar conditions, 1-methyl-2-(3-pyridyl)-3-(5-carboxypentyl)-5-chloroindole also potentiates the blood pressure lowering effect of libenzapril.

Further illustrative of the invention, potentiation of the blood pressure lowering effect of benazepril hydrochloride and captopril, administered intraarterically to spontaneous hypertensive rats at 0.1 mg/Kg/min and 0.2 mg/Kg/min, respectively is also observed after prior administration of 10 mg/Kg p.o of CGS 12970.

A significant aspect of the invention is the finding that the 2-(3-pyridyl)-indole derivatives as defined above enhance the antihypertensive effectiveness of angiotensin converting enzyme inhibitors at doses which are essentially devoid of antihypertensive activity.

The 2-(3-pyridyl)-indole derivatives as defined above are thus particularly useful as adjuvants to enhance the antihypertensive effectiveness of angiotensin converting enzyme inhibitor antihypertensive agents in mammals.

The effective dosage for achieving said potentiation or adjuvant effect is dependent on the species, weight, age and individual condition of the mammal host and on the form of administration. A unit dosage for oral administration to a mammal of about 50 to 70 Kg may contain between about 25 and 200 mg of a said 2-(3-pyridyl)-indole derivative as the adjuvant active ingredient to be used in combination with a suitable amount of the angiotensin converting enzyme inhibitor to be potentiated.

A unit dosage of the angiotensin converting enzyme inhibitor ranges between about 2.5 and 50 mg, such being dependent on the effective antihypertensive dose of the particular angiotensin converting enzyme inhibitor to be potentiated.

The following examples are intended to illustrate compositions useful in the new method according to this invention, and they are not to be construed as being limitations thereon.

EXAMPLE 1

| (A) 10,000 Capsules each containing the following: | |
| --- | --- |
| Libenzaprl | 250.0 g |
| 1-(7-carboxyheptyl)-3-methyl-2-(3-pyridyl)-indole | 500.0 g |
| Lactose | 1150.0 g |
| Talcum powder | 100.0 g |
| (B) 10,000 Capsules each containing the following: | |
| Benazepril Hydrochloride | 100.0 g |
| 1-(7-carboxyheptyl)-3-methyl-2-(3-pyridiyl)-indole | 250.0 g |
| Lactose | 1,550.0 g |
| Talcum powder | 100.0 g |

Procedure:

All the powders are passed through a screen with openings of 0.6 mm. Then the drug substances are placed in a suitable mixer and mixed first with the talcum, then with the lactose until homogenous. No. 3 capsules are filled with 200 mg, using a capsule filling machine.

What is claimed is:

1. A method of potentiating the antihypertensive effect of an angiotensin converting enzyme inhibitor in a mammal receiving an angiotensin converting enzyme inhibitor selected from the group consisting of benzepril, benazeprilat, libenzapril, and a pharmaceutically acceptable salt thereof, which comprises the administration to said mammal in combination with said enzyme inhibitor of an effective potentiating amount of 1-(7-carboxyheptyl)-3methyl-2-(3-pyridyl)-indole, 1-methyl-2-(3-pyridyl)-3-(5carboxypentyl)-5-chloroindole, or a pharmaceutically acceptable salt thereof, said effective antihypertensive potentiating amount being essentially devoid of antihypertensive activity.

2. A method according to claim 1 of potentiating the antihypertensive effect of an angiotensin converting enzyme inhibitor selected from the group consisting of benazepril, benazeprilat, libenzapril, and a pharmaceutically acceptable salt thereof, comprising the administration of an effective antihypertensive potentiating amount of 1-(7-carboxyheptyl)-3-methyl-2-(3-pyridyl)-indole or a pharmaceutically acceptable salt thereof, said effective potentiating amount being essentially devoid of antihypertensive activity.

3. A method according to claim 1 of potentiating the antihypertensive effect of an angiotensin converting enzyme inhibitor selected from the group consisting of benazepril, benazeprilat, libenzapril, and a pharmaceutically acceptable salt thereof comprising the administration of an effective antihypertensive potentiating amount of 1-methyl-2-(3-pyridyl)-3-(5-carboxypentyl)-5-chloroindole or a pharmaceutically acceptable salt thereof, said effective potentiating amount being essentially devoid of antihypertensive activity.

4. A method according to claim 1 of potentiating the antihypertensive effect of benazepril or a pharmaceutically acceptable salt thereof comprising the administration of an effective antihypertensive potentiating amount of 1-(7-carboxyheptyl-3-methyl-2-(3-pyridyl)-indole or a pharmaceutically acceptable salt thereof, said effective potentiating amount being essentially devoid of antihypertensive activity.

5. A method according to claim 1 of potentiating the antihypertensive effect of libenzapril or a pharmaceutically acceptable salt thereof comprising the administration of an effective antihypertensive potentiating amount of 1-(7-carboxyheptyl)-3-methyl-2-(3-pyridyl)-indole or a pharmaceutically acceptable salt thereof, said effective potentiating amount being essentially devoid of antihypertensive activity.

6. A method according to claim 1 of potentiating the antihypertensive effect of benazepril or a pharmaceutically acceptable salt thereof comprising the administration of an effective antihypertensive potentiating amount of 1-methyl-2-(3-pyridyl)-3-(5-carboxypentyl)-5-chloroindole or a pharmaceutically acceptable salt thereof, said effective potentiating amount being essentially devoid of antihypertensive activity.

7. A method according to claim 1 of potentiating the antihypertensive effect of libenzapril or a pharmaceutically acceptable salt thereof comprising the administration of an effective antihypertensive potentiating amount of 1-methyl-2-(3-pyridyl)-3-(5-carboxypentyl)-5-chloroindole or a pharmaceutically acceptable salt thereof, said effective potentiating amount being essentially devoid of antihypertensive activity.

8. A method of treating hypertension in a mammal which comprises administering to a mammal in need thereof a combination of
   (a) an effective antihypertensive amount of an angiotensin converting enzyme inhibitor selected from the group consisting of benazepril, benazeprilat and libenzapril, and a pharmaceutically acceptable salt thereof, and
   (b) 1-(7-carboxyheptyl)-3-methyl-2-(3-pyridyl)-indole or 1-methyl-2-(3-pyridyl)-3-(5-carboxypentyl)-5-chloroindole, or a pharmaceutically acceptable salt thereof, in an amount essentially devoid of antihypertensive activity and effective in enhancing the antihypertensive effect of said angiotensin converting enzyme inhibitor.

9. A method according to claim 8 of treating hypertension in a mammal which comprises administering to a mammal in need thereof a combination of
   (a) an effective antihypertensive amount of an angiotensin converting enzyme inhibitor selected from the group consisting of benazepril, benazeprilat and libenzapril, and a pharmaceutically acceptable salt thereof; and
   (b) 1-(7-carboxyheptyl)-3-methyl-2-(3-pyridyl)-indole or a pharmaceutically acceptable salt thereof in an amount essentially devoid of antihypertensive activity and effective in enhancing the antihypertensive effect of said angiotensin converting enzyme inhibitor.

10. A method according to claim 8 of treating hypertension in a mammal which comprises administering to a mammal in need thereof a combination of
    (a) an effective antihypertensive amount of an angiotensin converting enzyme inhibitor selected from the group consisting of benazepril, benazeprilat and libenzapril, and a pharmaceutically acceptable salt thereof, and
    (b) 1-methyl-2-(3-pyridyl)-3-(5-carboxypentyl)-5-chloroindole or a pharmaceutically acceptable salt thereof, in an amount essentially devoid of antihypertensive activity and effective in enhancing the antihypertensive effect of said angiotensin converting enzyme inhibitor.

11. A method according to claim 8 of treating hypertension in a mammal which comprises administering to a mammal in need thereof a combination of
    (a) an effective antihypertensive amount of benazepril or a pharmaceutically acceptable salt thereof, and
    (b) 1-methyl-2-(3-pyridyl)-3-(5-carboxypentyl)-5-chloroindole or a pharmaceutically acceptable salt thereof, in an amount essentially devoid of antihypertensive activity and effective in enhancing the antihypertensive effect of said angiotensin converting enzyme inhibitor.

12. A method according to claim 8 of treating hypertension in a mammal which comprises administering to a mammal in need thereof a combination of
    (a) an effective antihypertensive amount of benazepril or a pharmaceutically acceptable salt thereof, and
    (b) 1-(7-carboxyheptyl)-3-methyl-2-(3-pyridyl)-indole or a pharmaceutically acceptable salt thereof, in an amount essentially devoid of antihypertensive activity and effective in enhancing the antihypertensive effect of said angiotensin converting enzyme inhibitor.

13. A method according to claim 8 of treating hypertension in a mammal which comprises administering to a mammal in need thereof a combination of
    (a) an effective antihypertensive amount of libenzapril or a pharmaceutically acceptable salt thereof, and
    (b) 1-(7-carboxyheptyl)-3-methyl-2-(3-pyridyl)-indole or a pharmaceutically acceptable salt thereof, in an amount essentially devoid of antihypertensive activity and effective in enhancing the antihypertensive effect of said angiotensin converting enzyme inhibitor.

14. A method according to claim 8 of treating hypertension in a mammal which comprises administering to a mammal in need thereof a combination of
    (a) an effective amount of libenzapril or a pharmaceutically acceptable salt thereof, and
    (b) 1-methyl-2-(3-pyridyl)-3-(5-carboxypentyl)-5-chloroindole or a pharmaceutically acceptable salt thereof, in an amount essentially devoid of antihypertensive activity and effective in enhancing the antihypertensive effect of said angiotensin converting enzyme inhibitor.

15. A method according to claim 8 which comprises administering to a mammal of about 50 to 70 kg in need thereof a combination of
    (a) an amount between about 2.5 and 50 mg of an angiotensin converting enzyme inhibitor as defined in said claim, and
    (b) an amount between about 25 and 200 mg of 1-(7-carboxyheptyl)-3-methyl-2-(3-pyridyl)-indole or 1-methyl-2-(3-pyridyl)-3-(5-carboxypentyl)-5-chloroindole, or a pharmaceutically acceptable salt thereof.

16. A method according to claim 1 wherein the angiotensin converting enzyme inhibitor is administered at the lowest effective antihypertensive dose.

* * * * *